US011219715B2

(12) United States Patent
Gray et al.

(10) Patent No.: US 11,219,715 B2
(45) Date of Patent: Jan. 11, 2022

(54) INJECTING A SUPPLEMENTAL FLUID IN A CONDUIT TO DELIVER A PRIMARY FLUID

(71) Applicant: Ivenix, Inc., Amesbury, MA (US)

(72) Inventors: George W. Gray, North Andover, MA (US); Susan E. Niemeier, North Andover, MA (US); Jesse E. Ambrosina, Topsfield, MA (US); Benjamin G. Powers, Portsmouth, NH (US)

(73) Assignee: Ivenix, Inc., North Andover, MA (US)

( * ) Notice: Subject to any disclaimer, the term of this patent is extended or adjusted under 35 U.S.C. 154(b) by 859 days.

(21) Appl. No.: 15/834,821

(22) Filed: Dec. 7, 2017

(65) Prior Publication Data

US 2019/0175831 A1 Jun. 13, 2019

(51) Int. Cl.
*A61M 5/168* (2006.01)
*A61M 5/142* (2006.01)
*A61M 5/155* (2006.01)
*A61M 5/14* (2006.01)
*A61M 5/145* (2006.01)

(52) U.S. Cl.
CPC ...... *A61M 5/16827* (2013.01); *A61M 5/1409* (2013.01); *A61M 5/14224* (2013.01); *A61M 5/14593* (2013.01); *A61M 5/155* (2013.01); *A61M 5/16886* (2013.01); *A61M 2005/1402* (2013.01); *A61M 2005/1403* (2013.01); *A61M 2205/3331* (2013.01); *A61M 2205/3337* (2013.01); *A61M 2205/3379* (2013.01);
(Continued)

(58) Field of Classification Search
CPC .......... A61M 5/168; A61M 5/14; A61M 5/00; A61M 5/16886; A61M 5/007; A61M 5/172; A61M 5/16827; A61M 5/14224; A61M 5/14212; A61M 2005/1787; A61M 5/142; A61M 39/24; A61F 7/17
See application file for complete search history.

(56) References Cited

U.S. PATENT DOCUMENTS 4,710,166 A * 12/1987 Thompson ............ A61M 5/172
604/123
4,828,545 A * 5/1989 Epstein ............. A61M 5/14224
604/66
(Continued)

FOREIGN PATENT DOCUMENTS

CN 204017120 12/2014
WO WO 20100039662 4/2010

*Primary Examiner* — Nathan R Price
*Assistant Examiner* — Anh Bui
(74) *Attorney, Agent, or Firm* — Armis IP Law, LLC

(57) ABSTRACT

A controller controls a fluid pump to deliver primary fluid from a first source at a desired rate through a respective conduit to a recipient. The controller monitors a volume of the primary fluid injected into the conduit. Subsequent to injecting a predetermined amount of the primary fluid into the conduit, the controller i) discontinues injection of the primary fluid into the conduit and ii) injects a secondary fluid through the conduit to advance a remaining portion of the primary fluid in the conduit to the recipient. The controller advances the secondary fluid into the conduit until a desired amount of the primary fluid is delivered trough the conduit to the recipient. Injection of the secondary fluid to push the remaining portion of the primary fluid reduces waste associated with the primary fluid.

29 Claims, 10 Drawing Sheets

(52) U.S. Cl.
CPC ... *A61M 2205/502* (2013.01); *A61M 2205/52* (2013.01); *A61M 2205/6018* (2013.01)

(56) References Cited

U.S. PATENT DOCUMENTS

| | | | | |
|---|---|---|---|---|
| 4,857,056 | A * | 8/1989 | Talonn | A61M 5/1454 604/135 |
| 5,016,440 | A * | 5/1991 | Sager | F04B 49/02 417/429 |
| 5,219,331 | A * | 6/1993 | Vanderveen | A61M 5/152 604/132 |
| 5,707,365 | A * | 1/1998 | Haber | A61M 5/19 604/191 |
| 7,503,903 | B2 * | 3/2009 | Carlisle | A61M 5/1408 604/246 |
| 8,628,514 | B2 * | 1/2014 | Fago | A61M 39/10 604/533 |
| 8,876,756 | B2 * | 11/2014 | Carlisle | A61M 5/16881 604/66 |
| 9,433,734 | B2 * | 9/2016 | Ambrosina | A61M 5/1408 |
| 9,457,142 | B2 * | 10/2016 | Day | A61M 5/24 |
| 2010/0280486 | A1 * | 11/2010 | Khair | A61M 5/16886 604/506 |
| 2014/0025015 | A1 * | 1/2014 | Cross | A61M 5/3294 604/198 |
| 2014/0058333 | A1 * | 2/2014 | Cross | A61M 5/002 604/198 |
| 2015/0119709 | A1 * | 4/2015 | Coolidge | A61M 5/16854 600/432 |

\* cited by examiner

FLUID DELIVERY SETTING INFO.
192

RECIPIENT NAME: JOHN DOE
FLUID ORDER # 234567    DATE: JANUARY 21, 2017

PRIMARY FLUID (TO BE DELIVERED) = FLUID X, 15 mL

CONNECT SOURCE OF PRIMARY FLUID X TO LEFT CHANNEL OF PUMP

SECONDARY FLUID (TO FLUSH FLUID X) = FLUID Y, 15 mL

CONNECT SOURCE OF SECONDARY FLUID Y TO RIGHT CHANNEL OF PUMP

DELIVERY FLOW RATE FOR FLUID X = 1 mL PER MINUTE

...

CONDUIT CAPACITY INFO.
193

| CONDUIT ID | CAPACITY |
|---|---|
| XYZ11 | 5 mL |
| XYZ22 | 7.5 mL |
| XYZ33 | 10.0 mL |
| ... | ... |

FIG. 2

INJECTING A SUPPLEMENTAL FLUID IN A CONDUIT TO DELIVER A PRIMARY FLUID

BACKGROUND

Conventional techniques of delivering fluid to a recipient can include drawing fluid from a fluid source into a chamber of a fluid pump. After the chamber is filled, a respective fluid delivery system applies a pressure to the chamber causing the fluid in the chamber to be delivered to a corresponding patient. The rate at which the fluid is delivered to the recipient may vary depending upon the magnitude of pressure applied to the chamber. Eventually, after applying pressure to the chamber for a sufficient amount of time, all of the fluid in the chamber is delivered to the recipient.

Typically, a conduit through which fluid is delivered to a recipient must be primed to deliver fluid to the recipient. For example, a conduit may initially be filled with a gas such as air. Pumping the fluid into the tube primes the tube, displacing any air in the tube with the fluid to be dispensed.

After the conduit is primed with fluid, the fluid pump automatically pumps fluid from a corresponding source container through the conduit to the recipient. When the pump is stopped, either manually or programmatically, there is some volume of fluid left in the conduit between the pump and the recipient that is typically either not delivered or delivered at an incorrect rate.

BRIEF DESCRIPTION OF EMBODIMENTS

This disclosure includes the observation that conventional techniques of delivering fluid result in a certain amount of fluid waste or a danger to the patient if the undelivered fluid is subsequently delivered along with a fluid from a different fluid source. For example, as previously discussed, the conduit between a fluid pump and a recipient must be filled (primed) with a specified fluid prior to delivery of any of the specified fluid to a recipient. Subsequent to a respective delivery of specified fluid, when the fluid source is depleted of fluid, at least portion of specified fluid remains in a tube between the fluid pump and a respective recipient. The tube and corresponding remaining fluid in the tube are typically discarded together, resulting in a waste of at least a portion of the source fluid. This is undesirable, especially if the fluid is expensive, and will result in an under-infusion of the prescribed fluid.

Embodiments herein include novel approaches to delivering fluid to a recipient, reducing fluid waste, and/or ensuring that a proper dose has been delivered to a target recipient.

More specifically, in one embodiment, a controller controls a fluid pump to deliver primary fluid from a first source at a desired rate through a respective conduit to a recipient. During delivery, the controller monitors a volume of the primary fluid injected into the conduit. Subsequent to injecting a predetermined amount of the primary fluid into the conduit, and prior to delivery of a specified amount of fluid to the recipient, the controller i) discontinues injection of the primary fluid into the conduit and ii) injects a secondary fluid through the conduit to advance a remaining portion of the primary fluid in the conduit to the recipient. The controller advances the secondary fluid into the conduit at least until the specified (prescribed) amount of the primary fluid is delivered through the conduit to the recipient.

Embodiments herein are useful over the cited prior art. For example, measured injection of the secondary fluid to push the remaining portion of the primary fluid in the conduit to the recipient reduces waste associated with the primary fluid. In other words, instead of the remaining portion of fluid being thrown out with a pump and/or disposable tube set, embodiments herein include using a secondary fluid to advance any remaining portion of the fluid to a recipient.

These and other more specific embodiments are disclosed in more detail below.

Note that any of the resources as discussed herein can include one or more computerized devices, fluid delivery device, medical devices, infusion pumps, fluid delivery systems, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (such as a physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: control a fluid pump to inject a primary fluid into a conduit for delivery of the primary fluid to a recipient; monitor injection of the primary fluid into the conduit; and subsequent to delivering a predetermined amount of the primary fluid into the conduit: i) discontinue injection of the primary fluid into the conduit, and ii) inject a secondary fluid through the conduit to advance a remaining portion of the primary fluid in the conduit to the recipient The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for efficient delivery fluid to a downstream recipient. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty. For additional details and/or possible perspectives (permutations) of the invention(s), the reader is directed to the Detailed Description section and corresponding figures of the present disclosure as further discussed below.

BRIEF DESCRIPTION OF THE DRAWINGS

FIG. 2 is an example diagram illustrating fluid delivery setting information and conduit capacity information facilitating delivery of one or more fluids to a recipient according to embodiments herein.

Figure 1:
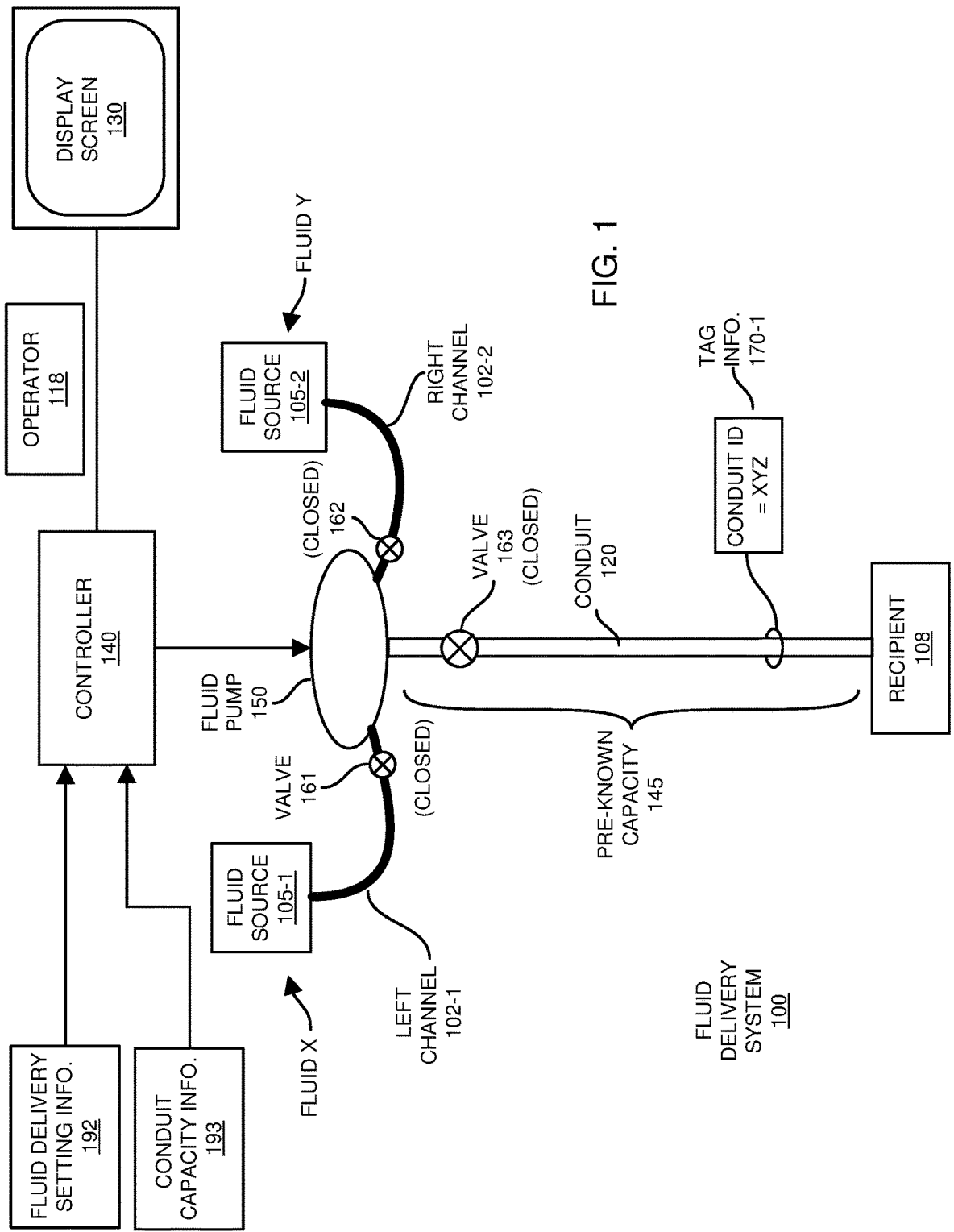
FIG. 1 is an example diagram illustrating a fluid delivery system according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

According to embodiments herein, a fluid delivery system (hardware and/or software) includes a fluid pump device to deliver fluid (such as fluid X) to a respective recipient at a desired flow rate. For example, the fluid pump device pumps the primary fluid X from source #1 at a desired rate into a respective conduit to the recipient. The controller monitors injection of the primary fluid X into the conduit. Subsequent to delivering a predetermined amount of the primary fluid X into the conduit: the controller discontinues injection of the primary fluid into the conduit and injects a secondary fluid through the conduit to advance a remaining portion of the primary fluid in the conduit to the recipient. The controller pushes the second fluid Y into the conduit until a desired amount of the primary fluid X is delivered through the conduit to the recipient.

As previously discussed, a common problem with conventional infusion devices is their inability to automatically deliver the entire volume of drug (such as medication), at the defined rate, to a patient. Infusion devices utilize administration sets (e.g., intravenous tubing) to move drugs from a fluid source, such as a bag of source, to the patient. Once the source empties, the infusion device stops, leaving some amount of drug in the administration set (tubing). The volume of fluid contained within the administration set, inclusive of the fluid between the pump's cassette and the IV catheter, or patient's blood stream, is known as the contained or dead volume.

Many expensive and/or highly reactive drugs are administered from source containers as small as 50 mL (milliliter). It is not uncommon for a typical disposable administration set to have a total contained volume of 10 mL. When the infusion is stopped due to an empty source container, as much as 20% of the drug is trapped in the tubing. A number drugs (e.g., antibiotics) need to reach threshold serum concentrations to achieve therapeutic effectiveness. If the administration set is discarded, the patient is, by definition, under-infused. Under infusion drug errors can lead to longer lengths of stay, additional drug costs due to waste and ultimately, irreversible harm.

A clinically correct workflow would be to replace the depleted fluid source with normal saline and program another short infusion at the original prescribed rate in order to deliver the remaining drug from the administration set to the patient. Unfortunately, a common practice is to replace the fluid source with normal saline or the next drug order and program the next infusion from a second fluid source at a rate different from what was prescribed for the original drug. In doing so, the clinician is unaware of the remaining contained drug in the tubing. The contained drug is accidentally delivered into the patient at an incorrect flow rate. For example, micro-infusion strategies have risen in popularity for critically ill patients in which the risk of fluid overload is a real concern. The drug solution is highly concentrated and it infuses at a lower rate. The potential risk of contained volume is magnified when a micro-infusion strategy is applied.

A similar problem exists when the infusion of drug is first started. Typically the administration set is initially primed with normal saline running at a given rate. The drug is then connected to the fluid path and a new dose rate is programmed for that drug. The dead volume in the administration set creates a lag between when the clinician starts the infusion of the drug and when that drug reaches the patient. During this time the normal saline is being infused at the rate programmed for the drug, which is often a rate lower than the rate at which the normal saline had been delivered prior to the start of the drug infusion.

In addition, when a drug is started or dose rate changed, there can be lag for the new concentration to reach the patient. The lag can lead to delays in intended dose delivery. Or, when a drug is discontinued, the delivery of the drug continues until the full contained volume is cleared from the tubing. A delay in the effect of the new drug can lead clinicians to increase the infusion to an excessive rate due to perceived inadequate dosage. They may inadvertently set drug delivery rates to harmful levels.

Embodiments herein include a system and method for delivering the contained drug at a preprogrammed rate by using the contents of a second fluid source to displace the contained volume and push the remaining drug to the patient. In order to accomplish this, the infusion device contained within this system is able to recognize the administration set under use, determine the contained volume of the tubing downstream from the device, detect whether a primary fluid source is already setup and provide the clinician with the option of delivering the remaining drug using fluid from the primary or a secondary fluid source. Embodiments herein further allow for the reduction of the initial delay between the infusion start and the time that the drug reaches the patient. This is accomplished by using knowledge of the contained volume to continue the infusion at the initial rate until the drug reaches the end of the administration set and then transitioning to the flow rate set for the drug.

Disclosed herein is an infusion system that enables users to deliver the entire therapy, including that which is contained in the administration set when the infusion is deemed complete. The infusion system also enables users to continue delivery of a previously running infusion at the previously configured rate until the new therapy reaches the patient.

This system is made up of an infusion device and a collection of one or more administration sets. Any one, or more, of these sets may be inserted into the infusion device to facilitate the delivery of medications, fluids and/or other infusates to a patient. Each administration set may contain information that identifies the set type or the contained volume of the set. This information may or may not be unique across distinct set types but shall, in some way, resolve to the volume of the set used. Set type and/or contained volume information may be contained within the set as by various means including, but not be limited to, RFID tags, bar codes, QR codes as well as any other visible or non-visible markings or means of physical identification. In one embodiment, the disposable tube set can be configured to include one or more physically protruding elements that contact a reader device. Depending on attributes of the protruding elements (such as number of elements, different length elements, etc.) as detected by the reader device, the reader device determines a unique identity of the type and corresponding volumetric capacity associated with the disposable tube set.

Additionally, note that users could have the option to enter the contained volume manually. This could be taken from the administration set packaging, and could also include additional downstream accessories, which can increase dead volume such as filters, manifolds and catheters.

The infusion device (fluid delivery system) as discussed herein can be configured to include one or more readers capable of retrieving the information associated with the administration sets (tubing, fluid pump, etc.). Upon insertion into the infusion device, the set type or contained volume of an administration set is read by a reader device of the fluid delivery system. If only set type information is provided, the infusion device shall derive the volume from a predefined lookup table indicating capacity associated with the disposable tube set that is being used to deliver fluid to a recipient. In either case, the contained volume will then be used by the infusion device in association with that loaded administration set (such as a disposable fluid assembly).

When administration sets that have no identifying information are used, the infusion device will prompt the user to enter the contained volume. This information may be known to the user or may be provided as documentation with the administration set. In accordance with certain embodiments, the operator of the fluid pump has the ability to modify capacity information associated with a disposable tube set as determined from a reader device that detects its type.

The infusion device (fluid delivery system) has the ability to control the flow of infusates to a patient from multiple sources. And, upon completion of the first infusion, automatically begin the administration of an already programmed infusion from a second source. A common application for this is to precede and follow the administration of a medication with hydration fluids such as normal saline. In this application, the medication from the first container is used to fill the contained volume at the rate the primary fluid is to be delivered. Once the contained volume is filled with the medication, the infusion then runs at the rate that was programmed for the medication. When the source container for the medication is empty, the fluid from the secondary container are then used to fill the contained volume at the rate the first medication was delivered. Once the contained volume is filled with the second fluid, the system continues delivery of the second fluid at the previously programmed rate.

During the programming of an infusion, the infusion device may provide the user with the option of delivering the entire contained volume. If this option is selected, the infusion device shall use a second infusate to displace the contained volume, pushing the contained volume of a first infusate to the patient. The infusion device may either push the remaining volume at the rate already programmed for the first infusate or may provide the option to deliver the volume at a different rate. The infusion device may also provide the option to follow the delivery of the contained volume with delivery of an infusate from the second fluid source at a new programmed rate. During the delivery of contained volume, the infusion device may provide some indication that the volume is being delivered and/or an indication of progress in the delivery of the contained volume. Upon completion of its delivery, the infusion device may optionally provide an indication that the contained volume has been delivered and the second infusate is currently being infused.

Likewise, during the programming of an infusion the infusion device may provide the user with the option of pre-priming the contained volume prior to delivery of the medication. If this option is selected, the infusion device shall continue infusing at the rate programmed for the fluid while the contained volume is filled with medication. Once the medication fills the contained volume the infusion device shall switch to infusing at the rate programmed for the medication. The infusion device may provide some indication that fluid is still being delivered and/or some indication of the progress of filling the contained volume with medication.

Now, more specifically, with reference to the figures, FIG. 1 is an example diagram illustrating a fluid delivery system according to embodiments herein.

As shown, fluid delivery system 100 includes fluid pump 150, controller 140, fluid source 105-1, and fluid source 105-2.

Fluid source 105-1 is connected to fluid pump 150 via the left channel 102-1 (conduit, fluid pathway, inlet, etc.). Fluid source 105-2 is connected to the fluid pump 150 via the right channel 102-2 (conduit, fluid pathway, inlet, etc.).

Note that fluid pump 150 (positive displacement pump such as a diaphragm pump, peristaltic fluid pump, etc.) can be any suitable type of device capable of pumping fluid through conduit 120 to the recipient 108.

In one embodiment, the fluid pump 150 is a diaphragm pump including flexible membrane 127 (such as made form elastically deformable material). Flexible membrane 127 divides the fluid pump 150 into chamber 130-1 and chamber 130-2. The controller 140 repeatedly monitors chamber 130-2 to determine and amount of fluid in the chamber 130-1. The controller 140 uses this information to control a flow rate of fluid inputted into conduit 120.

Figure 3:
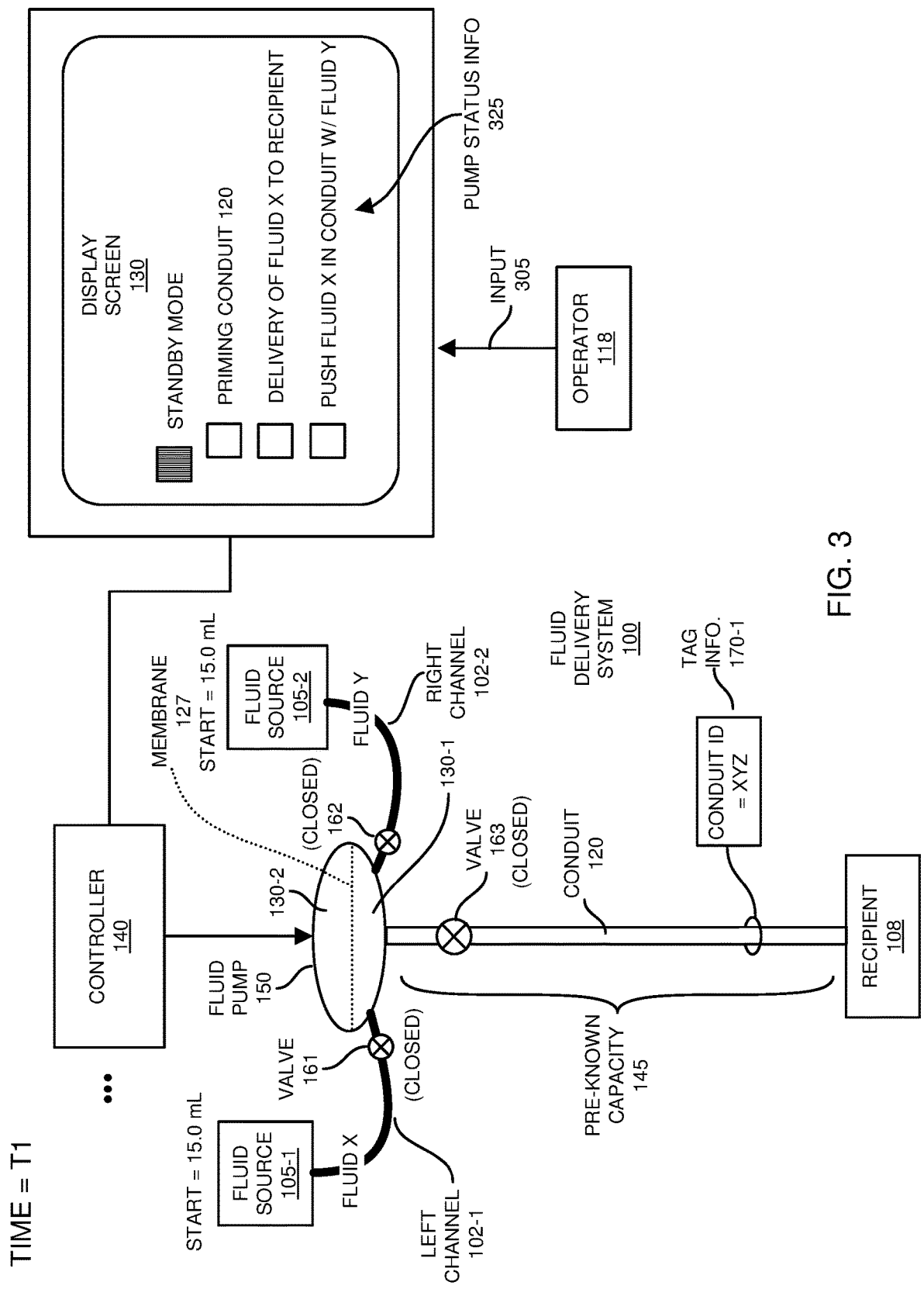
FIG. 3 is an example diagram illustrating programming of a fluid delivery system to deliver fluid as specified by an order according to embodiments herein.

With reference to FIG. 3, in addition to controlling gas pressure applied to chamber 130-2 to control a flow of fluid inputted into conduit 120, the controller 140 controls valve 161, valve 162, and valve 163 at appropriate times to draw respective fluid into the chamber 130-1 and then expel the fluid in the chamber 130-1 into the conduit 120 downstream to the recipient 108.

To draw primary fluid X from fluid source 105-1 into the chamber 130-1, while valves 162 and 163 are controlled to be closed and valve 161 is open, the controller 140 applies a negative pressure to the chamber 130-2 to draw fluid X into the chamber 130-1 from source 105-1.

Subsequent to filling the chamber 130-1, while the controller 140 controls each of the valves 161 and 162 to a respective closed state and controls the valve 163 to an open state, the controller 140 applies a positive gas pressure to chamber 130-2, causing the primary fluid X in chamber 130-1 to flow into conduit 120.

Via control of valves 161, 162, and 163, and gas pressure in chamber 130-2, the controller 140 precisely controls delivery of the primary fluid X from fluid source 105-1 at the desired rate into conduit 120. The controller 140 repeats this control cycle (drawing fluid into channel 130-1 and then expelling it) to deliver a desired amount of primary fluid X from fluid source 105-1 into the conduit 120.

Note that to draw secondary fluid Y from fluid source 105-2 into the chamber 130-1, the controller 140 controls valves 161 and 163 to be closed and valve 162 to be open. In this state, the controller 140 further applies a negative pressure to the chamber 130-2 to draw secondary fluid Y into the chamber 130-1. Subsequent to filling the chamber 130-1 with the secondary fluid Y, while the controller 140 further controls each of the valves 161 and 162 to a closed state and controls the valve 163 to an open state, the controller 140 applies a positive gas pressure to chamber 130-2 causing the secondary fluid Y in chamber 130-1 to flow into conduit 120.

The controller 140 precisely controls application of pressure to the chamber 130-2 to deliver the secondary fluid Y from fluid source 105-1 at the desired rate into conduit 120. The controller 140 repeats this control cycle to deliver a desired amount of primary fluid from fluid source 105-1 into the conduit 120.

Note that, as further discussed herein, capacity information associated with the conduit 120 (such as information indicating that the segment of conduit 120 has a volumetric capacity of 5 mL of fluid) serves as a basis to indicate how much of the fluid Y should be injected into the conduit 120 to complete delivery of fluid X to the recipient 108.

In one embodiment, the controller 140 receives input (such as from the pump operator 118, bar code reader, etc.) indicating tag information 170-1 assigned to the conduit 120 being used to deliver fluid to the recipient 108. Assume that the tag information 170-1 in this example embodiment indicates that conduit identifier value of XYZ11 is assigned to the conduit 120 (such as disposable tube set and fluid pump). Via the tag information 170-1, the controller 140 is able to identify the volumetric capacity (pre-known capacity 145) of conduit 120 (i.e., fluid pathway) between the fluid pump 150 and the recipient 108.

As further discussed below, the controller 140 uses the fluid delivery setting information 192 and conduit capacity information 193 to control delivery of one or more fluids to the recipient 108.

FIG. 2 is an example diagram illustrating fluid delivery setting information and conduit capacity information facilitating delivery of one or more fluids to a recipient according to embodiments herein.

In this example embodiment, assume that the fluid delivery system 100 is preprogrammed with conduit capacity information 193 or such information is available to the controller 140 in a remote repository or derived from previously stored information. In one embodiment, the controller 140 uses the conduit capacity information 193 to map the conduit identifier value XYZ11 as specified by the tag information 170-1 to a capacity of 5.0 mL. This mapping indicates to the controller 140 that the pre-known capacity 145 associated with conduit 120 (fluid pathway) between the fluid pump 150 and the recipient 108 is 5.0 mL.

Controller 140 also has access to the fluid delivery setting information 192. The fluid delivery setting information 192 can be stored locally in the fluid delivery system 100. Alternatively, the fluid delivery setting information 192 can be stored in a remote repository accessible by the controller 140.

In one embodiment, the fluid delivery setting information 192 represents a fluid delivery order indicating attributes of delivering fluid to the recipient 108.

In this example embodiment, fluid delivery setting information 192 indicates an identity (name) of the recipient 108. Additionally, the fluid delivery setting information 192 indicates a fluid order number and a date that the fluid is prescribed to the recipient (such as a patient, fluid storage device, etc.).

As shown, note that fluid delivery setting information 192 can be configured to include further information such as information indicating a rate (1 mL/minute) at which the primary fluid X is to be delivered to the recipient 108.

Yet further, the fluid delivery setting information 192 can be configured to indicate an identity of the primary fluid X (such as drug name, chemical name, etc., of fluid) to be delivered to the recipient 108 as well as a corresponding amount.

In this example embodiment, fluid delivery setting information 192 further indicates a secondary fluid such as fluid Y that is to be used to push any remaining portion of fluid X through the conduit 120 to the recipient 108. In other words, the fluid delivery setting information 192 indicates secondary fluid Y that is to be used to displace the remaining portion of the primary fluid X in the conduit to the recipient 108. Thus, in accordance with the fluid delivery setting information 192, the controller 140 utilizes the fluid delivery setting information 192 to detect that the secondary fluid Y is to be used to advance the remaining portion of the primary fluid X using the secondary fluid Y.

Note that embodiments herein can further include automatic programming of the fluid delivery system 100 to deliver fluid X to a recipient as specified by the fluid delivery setting information 192. In one embodiment, the fluid delivery setting information 192 indicates an order of inputting multiple fluids into the conduit 102. For example, the fluid delivery setting information 192 indicates to first input the primary fluid X into the conduit 120 followed by input of the secondary fluid Y into the conduit 120.

Thus, according to embodiments herein, the controller 140 receives fluid delivery setting information 192 associated with the primary fluid X to be delivered to the recipient 108. The fluid delivery setting information 192 indicates that the secondary fluid Y is to be used to advance the remaining portion of the primary fluid X during fluid delivery.

In accordance with further embodiments, the fluid delivery setting information 192 can be configured to indicate to connect the source 105-1 to the left channel 102-1. Additionally, the fluid delivery setting information 192 can be configured to indicate to connect the source 105-2 to the right channel 102-2. In accordance with the fluid delivery setting information 192, the controller 140 provides a humanly perceptible output such as a notification on display screen 130 to the operator 118 indicating to: i) couple the fluid source 105-1 of the primary fluid X to a left input channel 102-1 of the fluid pump 150 and ii) couple the fluid source 105-2 of the secondary fluid Y to the right input channel 102-2 of the fluid pump 150 as shown in FIG. 3. This ensures that the fluid sources 105 are connected to the appropriate channels in accordance with the fluid delivery setting information 192.

As further discussed herein, the controller 140 uses the flow rate information in fluid delivery setting information 192 (such as flow rate information indicating 1 mL/minute delivery rate) as specified by the fluid delivery setting information 192 to pump both the primary fluid X and the secondary fluid Y into the conduit 120. As further discussed below, controlling a rate of injecting the secondary fluid Y (such as the same rate of previously pumping fluid X) through the conduit 120 results in delivery of any remaining portion of the primary fluid X in the conduit 120 to the recipient 108 such that the full dose of primary fluid X (15 mL) is delivered to the recipient 108 at a desired flow rate (1 mL/minute).

FIG. 3 is an example diagram illustrating programming of a fluid delivery system to deliver fluid as specified by an order according to embodiments herein.

As shown, at time T1, the fluid delivery system 100 indicates that it is operating in the standby mode via respective humanly perceptible output (such as pump status information 325) displayed on display screen 130. Subsequent to connecting fluid source 105-1 to the left channel 102-1 and fluid source 105-2 to the right channel 102-2, assume that the operator 118 provides input 305 to start delivery of a respective fluid X to recipient 108.

Figure 4:
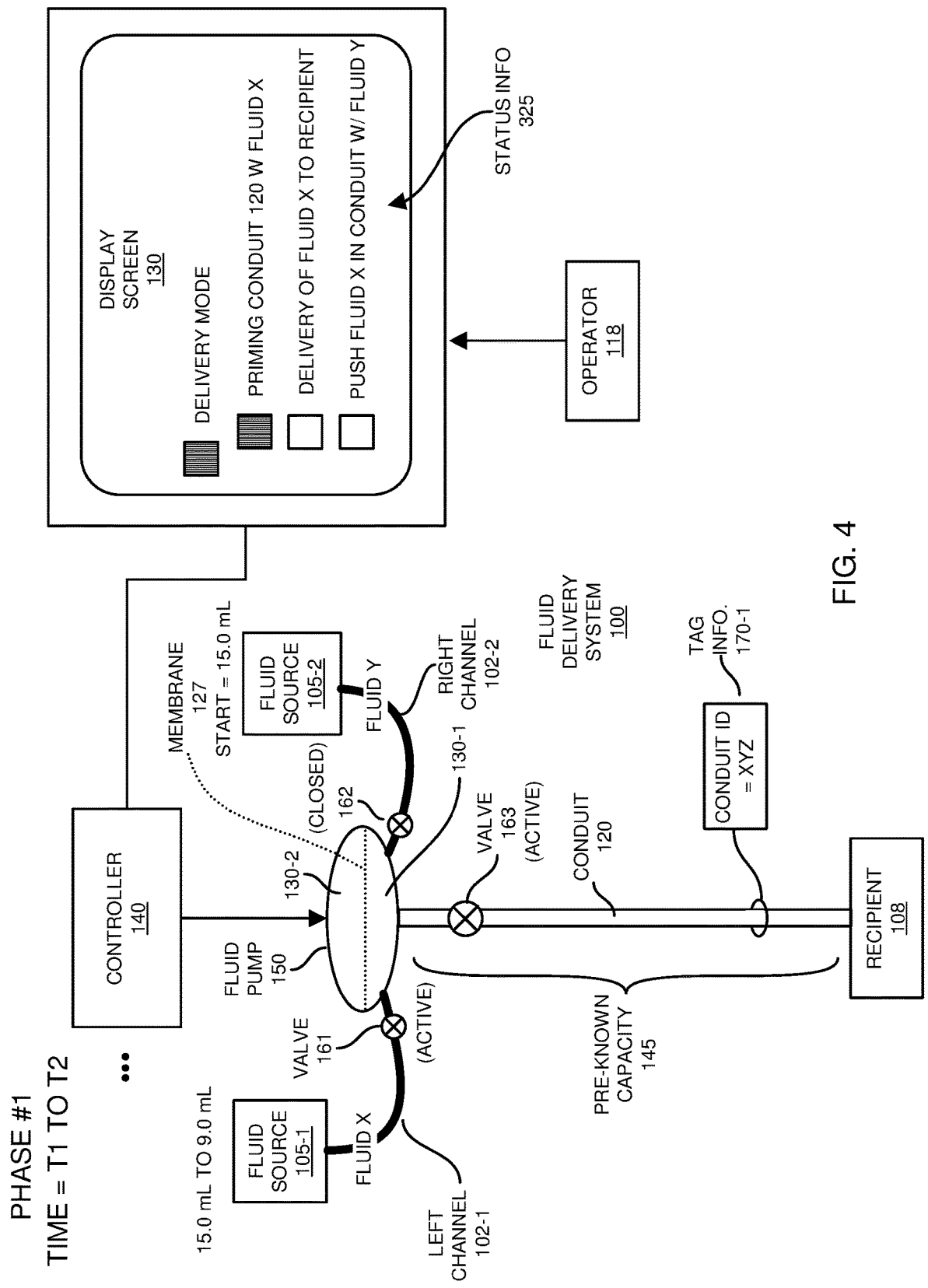
FIG. 4 is an example diagram illustrating a first phase of priming a respective conduit with a primary fluid according to embodiments herein.

FIG. 4 is an example diagram illustrating a first phase of priming a respective conduit with a primary fluid according to embodiments herein.

As shown, between time T1 and time T2, in a manner as previously discussed, the controller 140 draws fluid X from fluid source 105-1 into chamber 130-1. The controller 140 pushes the fluid X in chamber 130-1 into conduit 120 when valve 163 is controlled open. In a manner as previously discussed, the controller 140 repeats a cycle of drawing fluid X from fluid source 105-1 into chamber 130-1 and expelling such fluid to prime the conduit 120 with fluid X.

In accordance with further embodiments, the controller 140 measures the amount of fluid X inputted to the conduit 120. During phase #1, between time T1 and time T2, the controller 140 produces a humanly perceptible output (such as pump status information 325) such as a notification on display screen 130 that the fluid delivery system 100 is operating in a delivery mode in which the primary conduit 120 is being primed with fluid X from source 105-1. Accordingly, the operator 118 is informed of the progress of fluid X being inputted into the conduit 120 to displace any gas present in the conduit 120.

Note that the rate of priming the conduit 120 with fluid X can be any suitable value and differ with respect to a rate at which the fluid X is to be delivered to the recipient 108 subsequent to priming.

When the controller 140 detects that 5 mL of fluid X has been inputted to the conduit 120 around time T2, the priming of conduit 120 is complete. In other words, conduit 120 is filled with fluid X.

Figure 5:
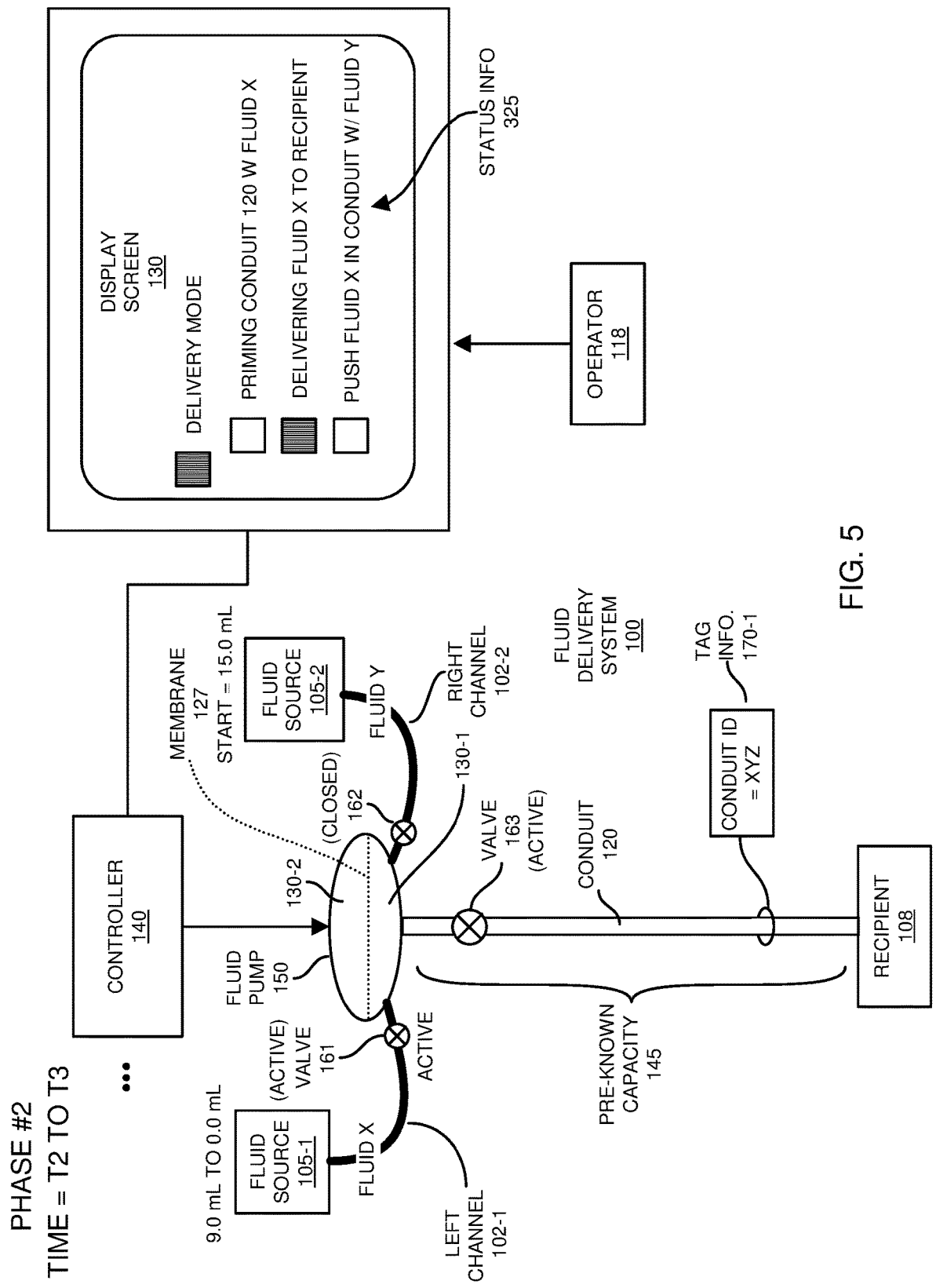
FIG. 5 is an example diagram illustrating a second phase of delivering a first portion of the primary fluid to a recipient according to embodiments herein.

FIG. 5 is an example diagram illustrating a second phase of delivering a first portion of the primary fluid to a recipient according to embodiments herein.

As shown, between time T2 and time T3 (phase #2), in a manner as previously discussed, the controller 140 draws fluid X from fluid source 105-1 into chamber 130-1. The controller 140 pushes the fluid X in chamber 130-1 into conduit 120 at a rate of 1 mL per minute as specified by the fluid delivery setting information 193.

The controller 140 measures the additional amount of fluid X inputted to the conduit 120 after priming.

As further shown, during phase #2, between time T2 and time T3, the controller 140 produces a humanly perceptible output (status information 325) such as a notification on display screen 130 indicating that the fluid delivery system 100 is operating in a delivery mode in which the primary conduit 120 is delivering fluid X to the recipient 108. Accordingly, the operator 118 is informed of the progress of fluid X being inputted into the conduit 120.

Figure 6:
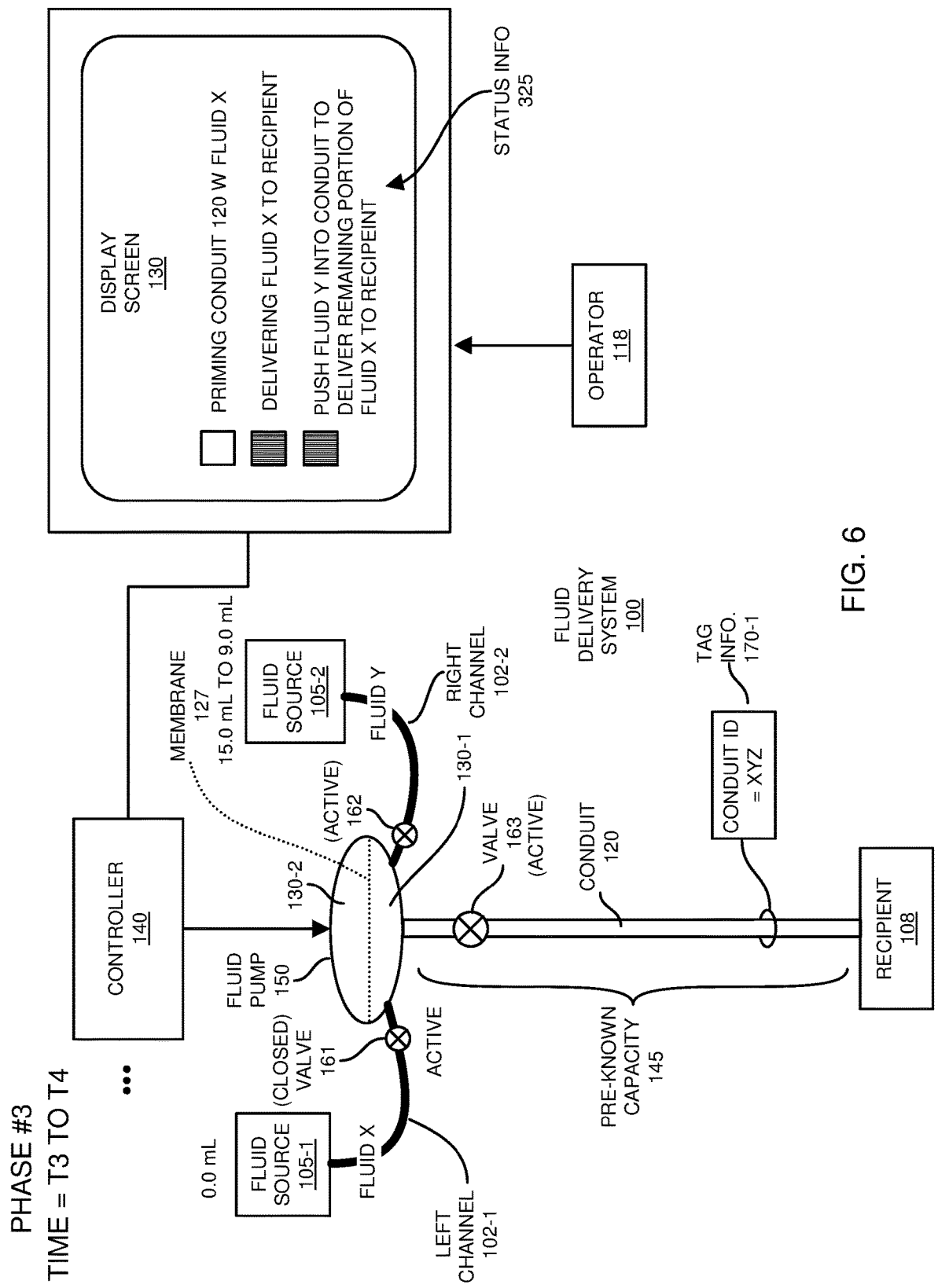
FIG. 6 is an example diagram illustrating a third phase of using a secondary fluid to deliver a remaining portion of the primary fluid in the conduit to a recipient according to embodiments herein.

In response to detecting (based on measurements by the controller 140) that the fluid pump 150 inputted the full 15 mL of fluid from fluid source 105-1 into the conduit 120, the controller 140 switches over to inputting fluid Y from fluid source 105-2 into fluid pump 150 and using the fluid Y outputted from the fluid pump 150 to push any remaining fluid X in conduit 120 to the recipient 108 as shown in phase #3 between time T3 and time T4 of FIG. 6.

In one embodiment, the controller 140 utilizes the fluid delivery setting information 192 to determine when the secondary fluid is to be used to advance the remaining portion of the primary fluid using the secondary fluid. For example, after depleting the fluid source 105-1 of the 15.0 mL and pumping it into conduit 120, the controller 140 knows to deliver an additional amount (5.0 mL) of secondary fluid Y as specified by the tag information 170-1 (and conduit identifier XYZ11) to the recipient 108 to push remaining portion of fluid X to the recipient 108.

FIG. 6 is an example diagram illustrating use of a secondary fluid to deliver a remaining portion of the primary fluid in the conduit to a recipient according to embodiments herein.

During operation in phase #3, in response to detecting that the amount of primary fluid X injected from the source 105-1 into the conduit 120 reaches a threshold value of inputting 15.0 mL into conduit 120 (in which 10 mL of the 15.0 mL has been delivered to recipient 108), the controller 140 discontinues attempting to inject the primary fluid (such as a first drug X from source 105-1) into the conduit 120. Because there is little or no more primary fluid X to pump, a 5 mL portion (based on pre-known capacity 145) of the primary fluid X remains in the conduit 120 at time T3.

To complete delivery of fluid X (such as the last 5.0 mL present in conduit 120 at time T3), the controller 140 operates the fluid pump 150 to inject a secondary fluid (fluid Y from source 105-2 as received over right channel 102-2)

through the conduit 120 to advance the remaining portion (5 mL) of the primary fluid X in the conduit 120 to the recipient 108.

Based on prior monitoring of delivering primary fluid X, the controller 140 knows that (full amount of 15.0—capacity of conduit, 5 mL) 10.0 mL of the primary fluid X has been delivered to the recipient 108 by time T3. Between time T3 and T4, while injecting the secondary (supplemental) fluid Y into the conduit 120, the controller 140 measures an amount of the secondary fluid (fluid Y from source #2) injected into the conduit 120 by the fluid pump 150. The controller 140 uses the measured amount of secondary fluid (fluid Y over channel 102-2 from source 105-2) injected into the conduit 120 as a basis to determine the additional amount of fluid X being delivered to the recipient 108 after the switchover.

As previously discussed, assume that the conduit 120 extending between the fluid pump 150 and the recipient 108 has a volumetric capacity of 5 mL (milliliters) as specified by the tag information 170-1 and conduit capacity information 193. Assume further in this example embodiment that the source 105-1 stores only 15 mL of drug X, all of which is to be delivered to the respective recipient 108.

Based on knowing that the conduit 120 has a capacity of 5 mL, as previously discussed, the controller 140 operates the fluid pump 150 to pump all 15 mL of the primary fluid (such as drug X, of chemical X, etc.) from source #1 into the conduit 120. Because there is no more fluid to pump from the source 105-1 other than the 15 mL, upon detecting that the fluid pump 150 has completed injection of 15 mL of drug X into the conduit 120 at time T3, the controller 140 operates the fluid pump 150 to pump 5 mL of fluid Y from source #2 into the conduit 120. The fluid Y injected into the conduit 120 pushes the remaining 5 mL of primary fluid X in the conduit to the recipient 108 at or around time T4. The controller 140 measures an amount of the secondary fluid Y injected into the conduit 120 during phase #3 and uses the measured amount of secondary fluid injected into the conduit 120 as a basis to calculate any additional amount (up to 5 mL) of the primary fluid X delivered to the recipient 108.

During phase #3, the controller 140 produces a humanly perceptible output such as a notification on the display screen 130 indicating that the fluid pump is currently delivering fluid X to the recipient via pumping of fluid Y into the conduit 120.

At time T4, the controller 140 discontinues injection of the secondary fluid Y into the conduit 120 in response to detecting that a predetermined amount of the secondary fluid Y (i.e., 5.0 mL, which corresponds to the capacity of conduit 120 as indicated by the tag information 170-1 and conduit capacity information 193) has been injected into the conduit 120.

Embodiments herein are useful because none (or only a very small amount) of the primary fluid X in source 105-1 (such as 15.0 mL) of fluid X is wasted as a result of not being delivered to the recipient 108 because the secondary fluid Y pushes the remaining portion of fluid X (5.0 mL) in the conduit to the recipient 108. In this manner, embodiments herein ensure that a full dose (15 mL) of specified fluid is delivered to the recipient 108, using two different fluids X and Y. For example, subsequent to switch over, as mentioned, the controller 140 uses the continued measurement of supplying the secondary fluid Y (5 mL) to determine a total amount of fluid X delivered to the recipient 108.

Figure 7:
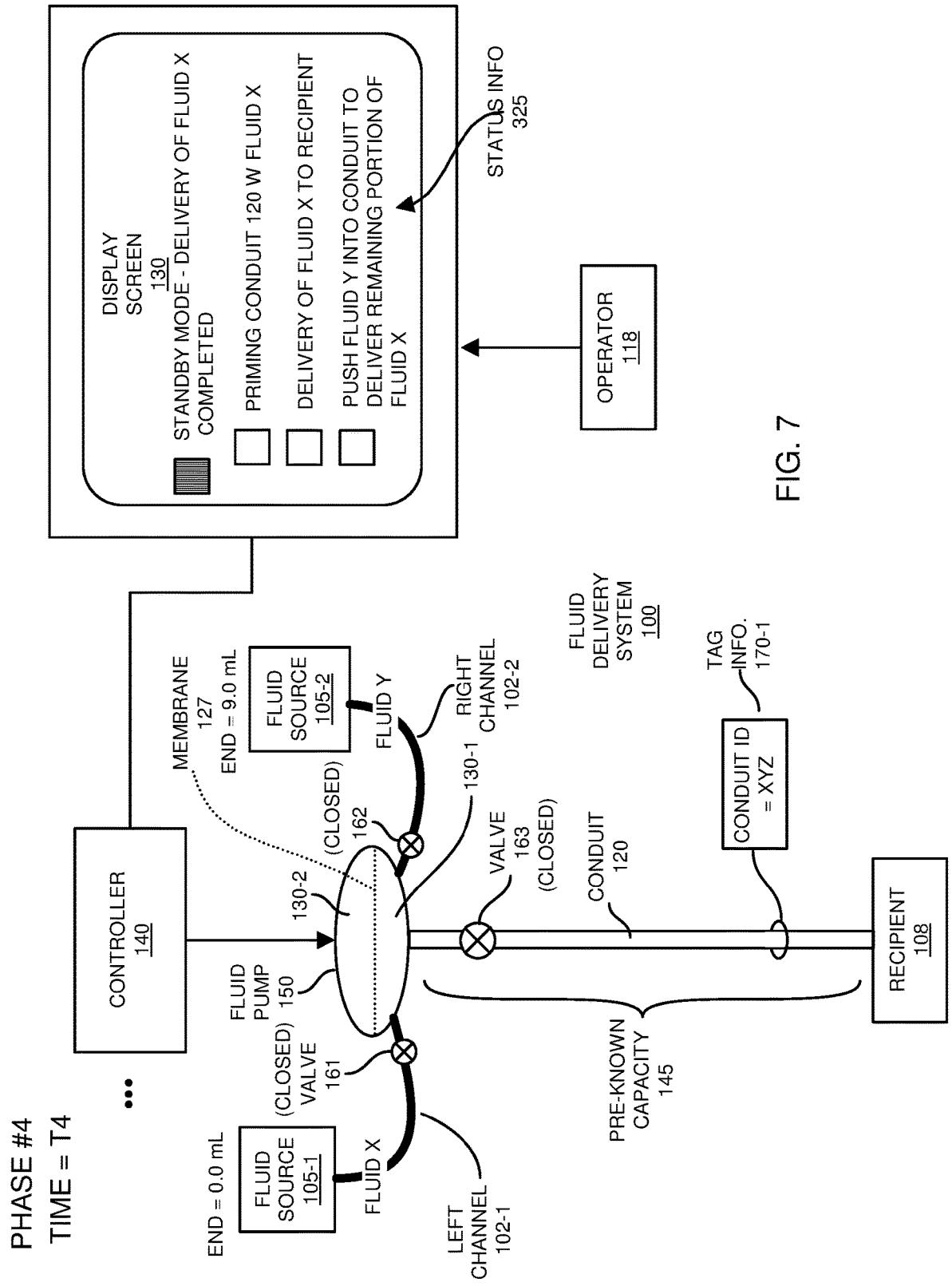
FIG. 7 is an example diagram illustrating completion of delivering the primary fluid to the recipient according to embodiments herein.

FIG. 7 is an example diagram illustrating completion of delivering the primary fluid to the recipient according to embodiments herein.

In one embodiment, as previously discussed, the controller 140 discontinues pumping fluid Y after it is known that a specified amount of fluid (such as a total of 15 mL of fluid X) has been delivered to the recipient 108.

In response to completing actual delivery of 15.0 mL of the fluid X to the recipient 108, the controller 140 produces a humanly perceptible output such as a respective notification to the operator 118 indicating completion of delivering the 15.0 mL of fluid X to the recipient 108.

Alternatively, if desired, note that the fluid pump 150 can be configured to continue pumping the fluid Y into the conduit 120 after time T4 to deliver any additional desired amount of fluid Y to the recipient 108.

Figure 8:
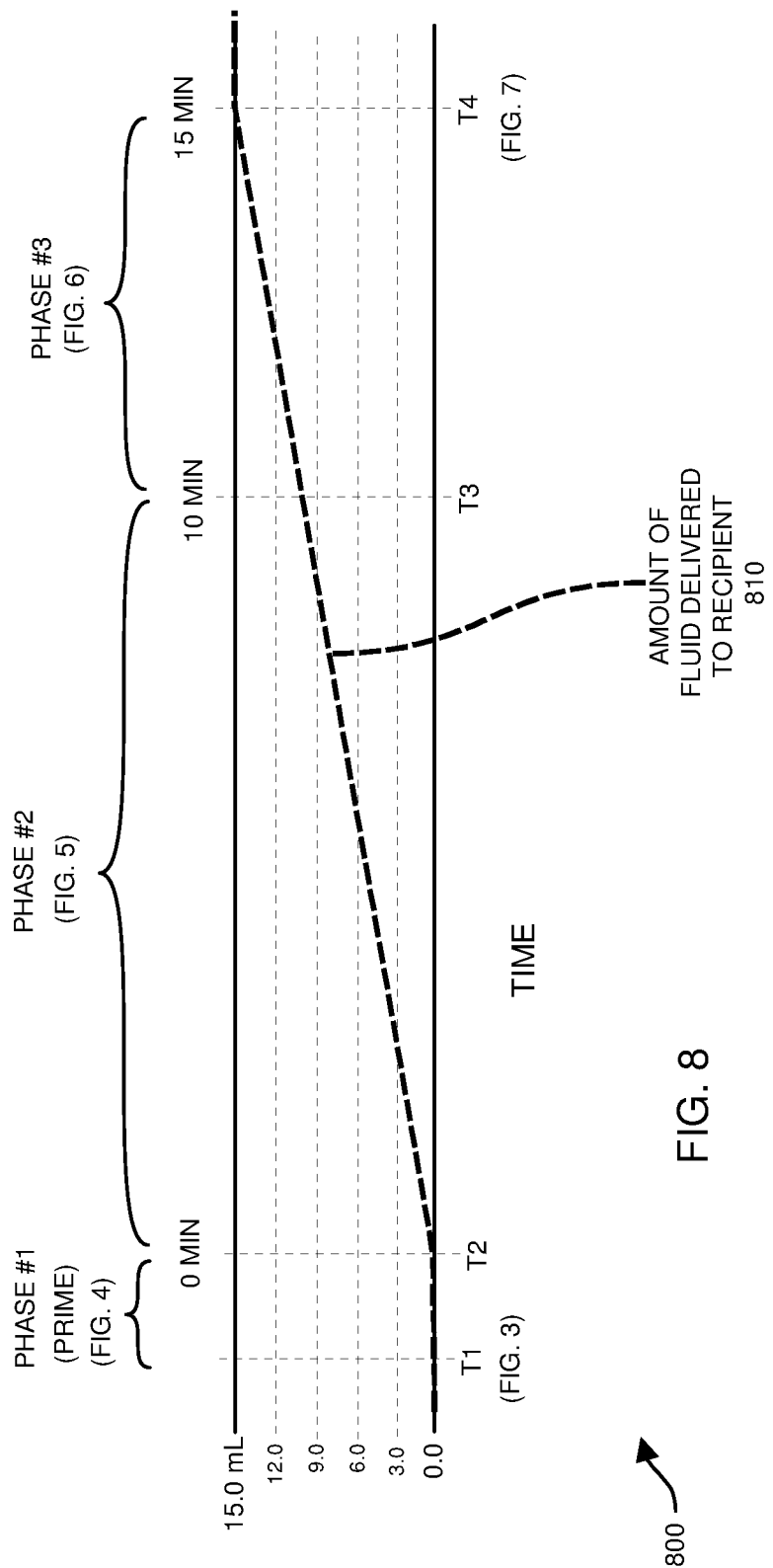
FIG. 8 is a timing diagram illustrating example delivery of one or more fluids at a constant flow rate to a recipient according to embodiments herein.

FIG. 8 is a timing diagram illustrating example delivery of one or more fluids to a recipient according to embodiments herein.

At time T1, the controller 140 controls display screen 130 to indicate (via a humanly perceptible output) that the fluid delivery system 100 is currently in standby mode in which no fluid has been delivered to a respective recipient 108.

Between time T1 and time T2, the controller 140 provides an indication (humanly perceptible output) such as on display screen 130 indicating that the fluid delivery system 100 is in a pre-delivery mode in which the fluid pump 150 is operated to prime conduit 120 with primary fluid X from fluid source 105-1. Fluid X is not yet delivered to the recipient 108 during the priming in phase #1. Thus, during phase #1, the controller 140 tracks delivery of the primary fluid inputted to the conduit 120 and provides notification to an operator 118 of the fluid pump 150 that the conduit 120 is being primed with the primary fluid X.

Subsequent to completion of priming the conduit 120 with the primary fluid X at time T2, the controller 140 provides notification (such as via a humanly perceptible output) to an operator 118 of the fluid pump 150 that the conduit 120 is now primed with the primary fluid X.

Between time T2 and time T3 (phase #2), the controller 140 provides an indication (humanly perceptible output) such as on display screen 130 indicating that the fluid delivery system 100 is in a delivery mode in which the fluid pump 150 is operated to pump fluid X from fluid source 105-1 into the conduit 120 to deliver primary fluid X to the recipient 108. Visual indicator 810 of timing diagram 800 indicates an amount of primary fluid X delivered to the recipient 108 over time.

At time T3, the controller 140 discontinues pumping fluid X from fluid source 105-1 into the conduit 120 because the fluid source 105-1 is now empty.

Between time T3 and time T4 (phase #3), the controller 140 switches over to pumping 5 mL of fluid Y into conduit 120 to push remaining portion (5.0 mL) of primary fluid X to the recipient 108. In one embodiment, during phase #3, the controller 140 provides an indication (humanly perceptible output) such as on display screen 130 indicating that the fluid delivery system 100 is in a delivery mode in which the fluid pump 150 inputs fluid Y into the conduit to push the remaining portion of fluid X to the recipient 108.

At time T4, the controller 140 discontinues pumping fluid Y from source 105-2 into the conduit 120 because the full dose (15 mL) of fluid X has been delivered to the recipient 108. At or around time T4, the controller 140 produces a humanly perceptible output (such as on display screen 130, audible tones, etc.) indicating completion of delivering the full dose of 15 mL to the recipient 108.

If desired, after time T4, the controller 140 operates the fluid pump 150 to continue infusing fluid Y into the recipient 108 through conduit 120.

In accordance with further embodiments, the controller 140 displays the timing diagram 800 and visual indication 810 on display screen 130 as status information 325 to provide notification of an amount of fluid X delivered to the recipient 108 over time. In one embodiment, the timing diagram 810 is continuously updated and displayed in substantially real-time to indicate the amount of primary fluid X delivered to the recipient 108 between time T2 and time T4. Thus, at any point time, the operator 118 (such as a caregiver) is able to determine an amount of the fluid X delivered to the recipient 108 (such as a patient).

Figure 9:
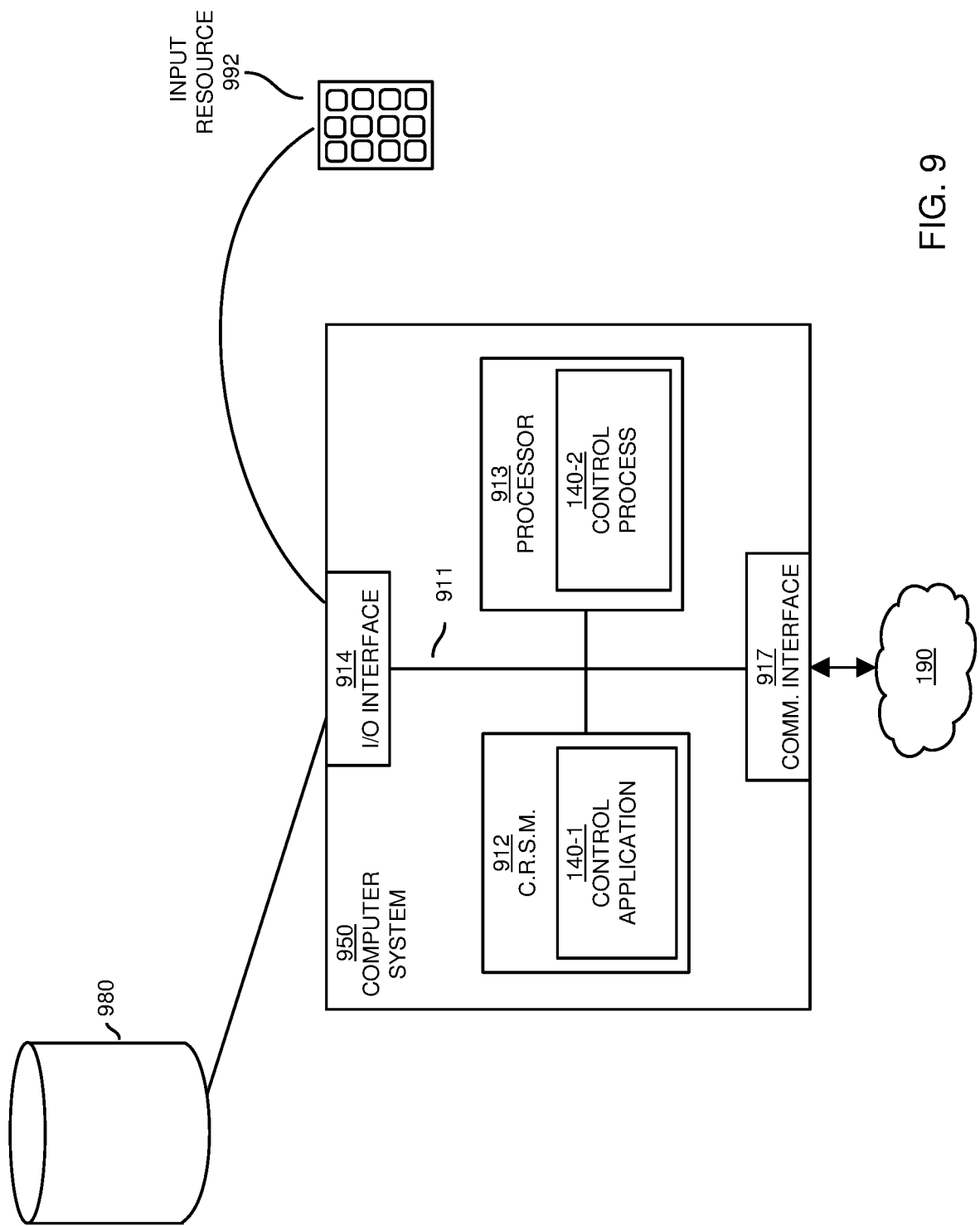
FIG. 9 is an example diagram illustrating a computer system in which to execute any of the functionality according to embodiments herein.

FIG. 9 is an example block diagram of a computer system for implementing any of the operations as discussed herein according to embodiments herein.

Any of the resources (such as controller 140, fluid delivery system 100, etc.) as discussed herein can be configured to include computer processor hardware and executable instructions to carry out any of the operations as discussed herein.

As shown, computer system 950 of the present example includes an interconnect 911 coupling computer readable storage media 912 such as a non-transitory type of media (such as a hardware storage medium) in which digital information can be stored and retrieved, a processor 913 (computer processor hardware), I/O interface 914, and a communications interface 917. I/O interface 914 supports connectivity to repository 980 and input resource 992.

Computer readable storage medium 912 (hardware to store instructions) can be any hardware storage device such as memory, optical storage, hard drive, floppy disk, etc. In one embodiment, the computer readable storage medium 912 stores instructions and/or data.

As shown, computer readable storage media 912 can be encoded with control application 140-1 (e.g., including instructions) associated with controller 140 to carry out any of the operations as discussed herein.

During operation of one embodiment, processor 913 accesses computer readable storage media 912 via the use of interconnect 911 in order to launch, run, execute, interpret or otherwise perform the instructions in control application 140-1 stored on computer readable storage medium 912. Execution of the control application 140-1 produces control process 140-2 to carry out any of the operations and/or processes as discussed herein.

Those skilled in the art will understand that the computer system 950 can include other processes and/or software and hardware components, such as an operating system that controls allocation and use of hardware resources to execute control application 140-1.

In accordance with different embodiments, note that computer system may be or included in any of various types of devices, including, but not limited to, a medical device, a fluid delivery pump, fluid delivery system, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, set-top box, content management device, handheld remote control device, any type of computing or electronic device, etc. The computer system 950 may reside at any location or can be included in any suitable resource in any network environment to implement functionality as discussed herein.

Functionality supported by the different resources will now be discussed via flowcharts in FIG. 10. Note that the steps in the flowcharts below can be executed in any suitable order.

Figure 10:
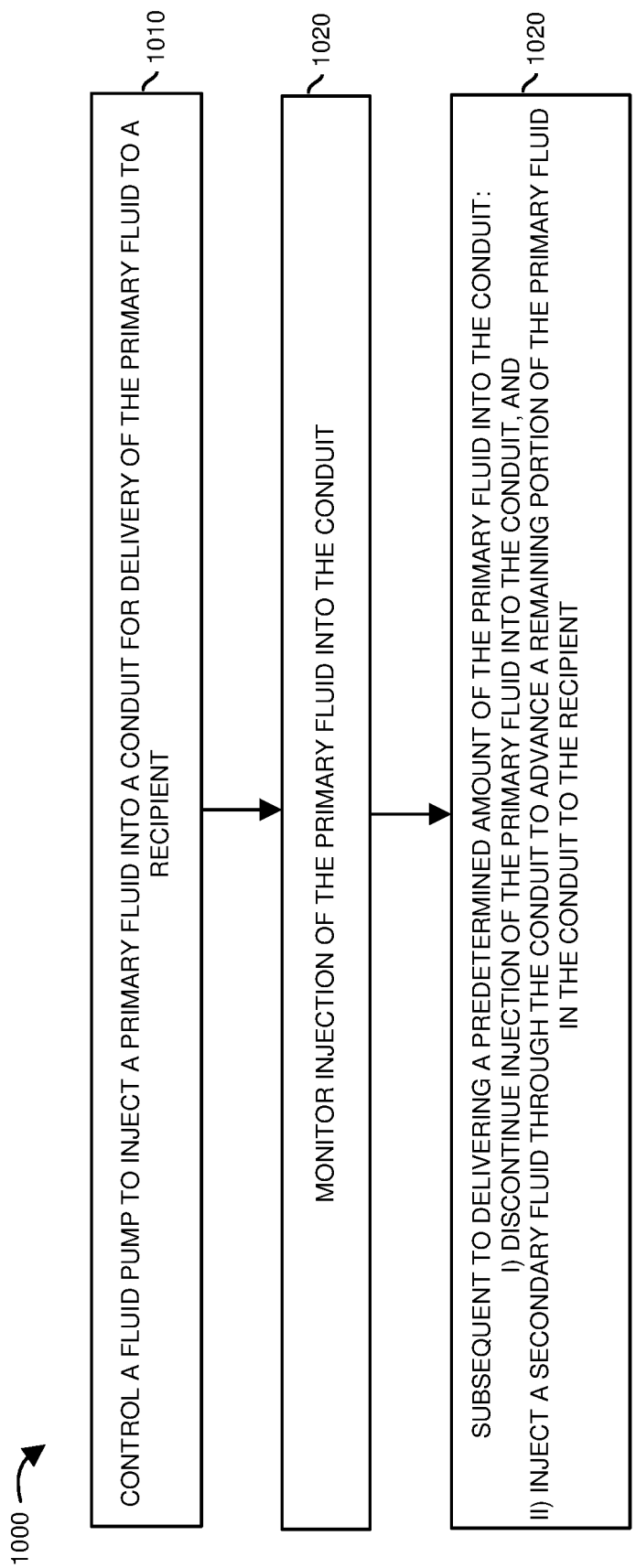
FIG. 10 is an example diagram illustrating a method according to embodiments herein.

FIG. 10 is a flowchart 1000 illustrating an example method according to embodiments. Note that there will be some overlap with respect to concepts as discussed above.

In processing operation 1010, the controller 140 (such as via execution of control application 140-1 or other hardware and/or software controller circuitry) controls a fluid pump 150 to inject a primary fluid X into a conduit 120 for delivery of the primary fluid X to a recipient 108.

In processing operation 1020, the controller 140 monitors injection of the primary fluid X into the conduit 120.

In processing operation 1030, subsequent to delivering a predetermined amount of the primary fluid X into the conduit 120: the controller 140 i) discontinues injection of the primary fluid X into the conduit 120, and ii) injects a secondary fluid Y through the conduit 120 to advance a remaining portion of the primary fluid X in the conduit 120 to the recipient 108.

Note again that techniques herein are well suited for controlling a flow of fluid from a fluid source to a recipient and reducing waste. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A system comprising:
    a fluid pump;
    a conduit disposed between the fluid pump and a recipient; and
    a controller operable to:
        control the fluid pump to inject a primary fluid into the conduit for delivery of the primary fluid to the recipient;
        measure an amount of the primary fluid injected into the conduit; and
        subsequent to injecting the measured amount of the primary fluid into the conduit: i) discontinue injection of the primary fluid into the conduit, ii) inject a secondary fluid through the conduit to advance a remaining portion of the primary fluid in the conduit to the recipient, and iii) measure an amount of the secondary fluid injected into the conduit subsequent to injecting the measured amount of the primary fluid into the conduit.

2. The system as in claim 1, wherein the controller is further operable to:
    control a rate of injecting the secondary fluid into the conduit to deliver the remaining portion of the primary fluid in the conduit to the recipient at a desired flow rate, the secondary fluid displacing the remaining portion of the primary fluid in the conduit to the recipient at the desired flow rate.

3. The system as in claim 2, wherein the controller is further operable to:
    discontinue injection of the secondary fluid into the conduit in response to detecting that the measured amount of the secondary fluid has been injected into the conduit.

4. The system as in claim 1, wherein the controller is further operable to:
    use the measured amount of secondary fluid injected into the conduit over time as a basis to calculate an amount of the remaining portion of the primary fluid in the conduit delivered to the recipient.

5. The system as in claim 1, wherein the controller is further operable to:
    receive a first input value indicating a quantity of fluid to deliver to the recipient;
    receive a second input value indicating a volumetric capacity of the conduit between the fluid pump and the recipient; and
    utilize the first input value and the second input value to control delivery of the primary fluid to the recipient.

6. The system as in claim 1, wherein the controller is further operable to:
    receive an input value assigned to the conduit, the input value indicating a capacity of the conduit between the fluid pump and the recipient; and
    utilize the input value to control delivery of the secondary fluid through the conduit to deliver the primary fluid to the recipient.

7. The system as in claim 6, wherein the controller is further operable to:
    retrieve the input value indicating the capacity of the conduit.

8. The system as in claim 1, wherein the controller is further operable to:
    receive fluid delivery setting information associated with the primary fluid to be delivered to the recipient, the fluid delivery setting information indicating that the secondary fluid is to be used to advance the remaining portion of the primary fluid during fluid delivery.

9. The system as in claim 1, wherein the controller is further operable to:
    track delivery of the first fluid through the conduit; and
    provide notification to an operator of the fluid pump that the conduit is currently being injected with the primary fluid.

10. The system as in claim 9, wherein the controller is further operable to:
    subsequent to completion of injecting the primary fluid into the conduit, provide notification to the operator of the fluid pump that the conduit is primed with the primary fluid.

11. The system as in claim 1, wherein the controller is further operable to:
    subsequent to injecting the conduit with the measured amount of the primary fluid, control a flow rate of injecting the secondary fluid into the conduit as specified by fluid delivery setting information assigned to the delivery.

12. The system as in claim 1, wherein the conduit is one of multiple different types of conduits available to deliver fluid from the fluid pump, the controller further operable to:
    receive an indication of a type assigned to the conduit.

13. The system as in claim 1, wherein the controller is further operable to:
    receive fluid delivery setting information indicating an order of inputting fluid into the conduit, the order indicating to first input the primary fluid into the conduit followed by input of the second fluid into the conduit.

14. The system as in claim 13, wherein the controller is further operable to:
    utilize the fluid delivery setting information to determine when the secondary fluid is to be used to advance the remaining portion of the primary fluid in the conduit to the recipient via injection of the secondary fluid into the conduit.

15. A method comprising:
    controlling a fluid pump to inject a primary fluid into a conduit for delivery of the primary fluid to a recipient, the conduit disposed between the fluid pump and the recipient;
    measuring an amount of the primary fluid infected into the conduit; and
    subsequent to delivering a predetermined amount of the primary fluid into the conduit:
        i) discontinuing injection of the primary fluid into the conduit,
        ii) injecting a secondary fluid through the conduit to advance a remaining portion of the primary fluid in the conduit to the recipient, and iii) measuring an amount of the secondary fluid injected into the conduit subsequent to injecting the measured amount of the primary fluid into the conduit.

16. The method as in claim 15 further comprising:
using the measured amount of secondary fluid injected into the conduit as a basis to calculate an amount of the primary fluid delivered to the recipient.

17. Computer-readable storage hardware having instructions stored thereon for execution, such that the instructions, when executed by computer processor hardware, cause the computer processor hardware to:
control a fluid pump to inject a primary fluid into a conduit for delivery of the primary fluid to a recipient, the conduit disposed between the fluid pump and the recipient;
measure an amount of the primary fluid injected into the conduit; and
subsequent to delivering a predetermined amount of the primary fluid into the conduit:
i) discontinue injection of the primary fluid into the conduit,
ii) inject a secondary fluid through the conduit to advance a remaining portion of the primary fluid in the conduit to the recipient; and
iii) measure an amount of the secondary fluid injected into the conduit subsequent to injecting the measured amount of the primary fluid into the conduit.

18. The system as in claim 1, wherein the controller is further operative to:
provide notification to an operator of the fluid pump of multiple different modes of delivering the primary fluid to the recipient via controlled injection of the primary fluid and the secondary fluid into the conduit.

19. The system as in claim 18, wherein the multiple different modes include:
i) a first mode in which the conduit is being primed and no portion of the primary fluid is delivered to the recipient,
ii) a second mode in which the conduit outputs the primary fluid from the conduit via injection of the primary fluid into the conduit, and
iii) a third mode in which the conduit outputs the primary fluid from the conduit via injection of the secondary fluid into the conduit.

20. The system as in claim 1, wherein the controller is further operative to:
calculate a total amount of the primary fluid delivered to the recipient based on the measured secondary fluid injected into the conduit.

21. The system as in claim 1, wherein the controller is further operative to:
calculate a total amount of the primary fluid delivered to the recipient based on the measured amount of the primary fluid injected into the conduit and the measured secondary fluid injected into the conduit.

22. The system as in claim 1, wherein the controller is further operative to:
inject the primary fluid into the conduit at a first flow rate during priming of the conduit with the primary fluid in a first mode in which no primary fluid is delivered through the conduit to the recipient; and
inject the primary fluid into the conduit at a second flow rate after priming of the conduit with the primary fluid in a second mode in which the primary fluid is delivered through the conduit to the recipient, the second flow rate different than the first flow rate.

23. The system as in claim 22, wherein the second flow rate is less than the first flow rate.

24. The system as in claim 1, wherein the controller is further operative to:
discontinue injection of the secondary fluid into the conduit in response to detecting delivery of a quantity of the primary fluid to the recipient as specified by a fluid delivery order.

25. The system as in claim 1, wherein the controller is further operative to:
calculate a total amount of the primary fluid delivered to the recipient based on a volumetric capacity of the conduit.

26. The system as in claim 1, wherein the controller is further operative to:
inject the primary fluid at a first flow rate; and
subsequent to injecting the measured amount of the primary fluid into the conduit, inject the secondary fluid into the conduit at the first flow rate.

27. The system as in claim 1, wherein the controller is further operative to:
initiate display of a visual indicator on a display screen, the visual indicator indicating the amount of the primary fluid delivered from the conduit to the recipient over time.

28. The system as in claim 27, wherein the controller is further operative to:
display timing information indicating a flow rate of delivering the primary fluid to the recipient during injection of the secondary fluid into the conduit.

29. The system as in claim 1, wherein the controller is further operative to:
switchover to injecting the secondary fluid into the conduit in response to detecting injection of the measured amount of the primary fluid into the conduit.

* * * * *

UNITED STATES PATENT AND TRADEMARK OFFICE
CERTIFICATE OF CORRECTION

PATENT NO. : 11,219,715 B2
APPLICATION NO. : 15/834821
DATED : January 11, 2022
INVENTOR(S) : George W. Gray et al.

Page 1 of 1

It is certified that error appears in the above-identified patent and that said Letters Patent is hereby corrected as shown below:

In the Claims

Column 16, Line 59, Claim 15 delete "infected" and insert --injected--

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*